(12) United States Patent
Sakata et al.

(10) Patent No.: US 10,292,602 B2
(45) Date of Patent: May 21, 2019

(54) BLOOD FLOW INDEX CALCULATING METHOD, BLOOD FLOW INDEX CALCULATING APPARATUS, AND RECORDING MEDIUM

(71) Applicant: FUJITSU LIMITED, Kawasaki-shi, Kanagawa (JP)

(72) Inventors: Masato Sakata, Isehara (JP); Daisuke Uchida, Atsugi (JP); Akihiro Inomata, Atsugi (JP); Hidenori Sekiguchi, Hadano (JP)

(73) Assignee: FUJITSU LIMITED, Kawasaki (JP)

( * ) Notice: Subject to any disclaimer, the term of this patent is extended or adjusted under 35 U.S.C. 154(b) by 752 days.

(21) Appl. No.: 14/862,402

(22) Filed: Sep. 23, 2015

(65) Prior Publication Data

US 2016/0007865 A1     Jan. 14, 2016

Related U.S. Application Data

(63) Continuation of application No. PCT/JP2013/059778, filed on Mar. 29, 2013.

(51) Int. Cl.
    *A61B 5/021*         (2006.01)
    *A61B 5/00*          (2006.01)
    *A61B 5/026*         (2006.01)
    *G06T 7/00*          (2017.01)
    *A61B 5/11*          (2006.01)

(52) U.S. Cl.
    CPC ........ *A61B 5/02125* (2013.01); *A61B 5/0077* (2013.01); *A61B 5/0261* (2013.01);
    (Continued)

(58) Field of Classification Search
    CPC ............ A61B 5/02007; A61B 5/02125; A61B 5/0285; A61B 5/0059; A61B 5/0261; A61B 5/6826; A61B 2576/00
See application file for complete search history.

(56) References Cited

U.S. PATENT DOCUMENTS 5,316,008 A     5/1994   Suga et al.
2008/0306372 A1*   12/2008   Ohki .................... A61B 5/0059
                                                            600/407

(Continued)

FOREIGN PATENT DOCUMENTS

EP          2631874 A1     8/2013
EP          2893872        7/2015

(Continued)

OTHER PUBLICATIONS

International Search Report and Written Opinion of the International Searching Authority (Form PCT/ISA/210, Form PCT/ISA/237), mailed in connection with PCT/JP2013/059778 and dated Jul. 9, 2013, with partial English translation (10 pages).

(Continued)

*Primary Examiner* — Christopher Koharski
*Assistant Examiner* — Pamela M. Bays
(74) *Attorney, Agent, or Firm* — Fujitsu Patent Center

(57) ABSTRACT

A blood flow index calculating method includes: obtaining, by a camera, an image capturing a first site of a living body and a second site of the living body; extracting an area of the first site of the living body and an area of the second site of the living body, by a processor; detecting a pulse wave pattern of the first site of the living body from the area of the first site of the living body and detecting a pulse wave pattern of the second site of the living body from the area of the second site of the living body, by the processor; first calculating a delay amount from the pulse wave pattern of the first site and the pulse wave pattern of the second site, by the processor; and second calculating an index related to blood flow by using the delay amount, by the processor.

12 Claims, 11 Drawing Sheets

(52) U.S. Cl.
CPC .......... *A61B 5/1128* (2013.01); *A61B 5/6826* (2013.01); *A61B 5/6898* (2013.01); *G06T 7/0016* (2013.01); *A61B 2576/00* (2013.01); *G06T 2207/30104* (2013.01)

(56) References Cited

U.S. PATENT DOCUMENTS

| | | | | |
|---|---|---|---|---|
| 2009/0076398 | A1* | 3/2009 | Li | A61B 5/021 600/494 |
| 2011/0251493 | A1 | 10/2011 | Poh et al. | |
| 2013/0046192 | A1* | 2/2013 | Lin | A61B 5/02007 600/500 |

FOREIGN PATENT DOCUMENTS

| | | |
|---|---|---|
| JP | 62-034531 | 2/1987 |
| JP | 04-200439 | 7/1992 |
| JP | 2006-247221 | 9/2006 |
| JP | 2007-319246 | 12/2007 |
| JP | 2008-301915 | 12/2008 |
| JP | 2009-247733 | 10/2009 |

OTHER PUBLICATIONS

EESR—The Extended European Search Report dated Mar. 15, 2016 for corresponding European Patent Application No. 13880373.9. **US2008/306372 cited in the above listed EESR was previously submitted in the IDS filed Sep. 23, 2015.
Jia Zheng, et al., "A remote approach to measure blood perfusion from the human face", Proceeding of SPIE, Jan. 1, 2009, pp. 716917-716917-7, vol. 7169, XP055016740. [cited in EESR dated March 15, 2016 for corresponding EP Application No. 13880373.9].
EPOA—Office Action of European Patent Application No. 13 880 373.9 dated Jan. 11, 2019.

* cited by examiner

BLOOD FLOW INDEX CALCULATING METHOD, BLOOD FLOW INDEX CALCULATING APPARATUS, AND RECORDING MEDIUM

CROSS-REFERENCE TO RELATED APPLICATION

This application is a continuation application of International Application PCT/JP2013/059778, filed on Mar. 29, 2013, and designating the U.S., the entire contents of which are incorporated herein by reference.

FIELD

The present invention relates to a blood flow index calculating method, a blood flow index calculating program, and a blood flow index calculating apparatus.

BACKGROUND

As a part of health care, measurement of pulse wave velocity and blood pressure is conducted. For example, when blood pressure is measured, a cuff is fitted around the arm of a subject, the artery is blocked by the arm being pressed with the cuff, and thereafter, blood pressure is measured by use of vibrations caused in the blood vessel wall as the cuff is depressurized.

However, the manometer has drawbacks that, for example, the many steps for measuring blood pressure are troublesome, the device itself is large and difficult to be always carried, and the measurement of blood pressure is burdensome since the arm is pressurized in the measurement.

Therefore, aiming to improve the user-friendliness, for example, a wrist watch type blood pressure measuring device has been proposed. In the wrist watch type blood pressure measuring device, the function of measuring blood pressure is incorporated into a wrist watch that is small sized and carried around on a daily basis. The wrist watch type blood pressure measuring device is fitted around the left wrist, and a finger tip of the right hand is placed on a front face portion where a phototransistor and an electrocardiographic wave detecting electrode, which is an electrode for detecting electrocardiographic waves, are provided side by side. The wrist watch type blood pressure measuring device detects electrocardiographic waves from the fingertip of the right hand placed on the electrocardiographic wave detecting electrode and the left wrist contacting the electrocardiographic wave detecting electrode, and detects finger pulse waves from blood flow in the fingertip of the right hand placed on the phototransistor. The wrist watch type blood pressure measuring device then measures a delay time from the detection of the electrocardiographic waves to the detection of the finger pulse waves, and calculates the blood pressure based on the delay time.

Patent Document 1: Japanese Laid-open Patent Publication No. 04-200439
Patent Document 2: Japanese Laid-open Patent Publication No. 2007-319246

However, by the above described techniques, blood pressure is unable to be measured without extra hardware.

For example, the wrist watch type blood pressure measuring device measures the delay time between the electrocardiographic waves and the finger pulse waves by using dedicated hardware, such as the electrocardiographic wave detecting electrode or the phototransistor, which is not installed in a general wrist watch. Therefore, by the wrist watch type blood pressure measuring device, without the installation of the dedicated hardware, the delay time is unable to be measured and blood pressure found from the delay time is also unable to be measured.

The measurement of blood pressure has been described above, but similarly, pulse wave velocity found from the delay time is also unable to be measured without dedicated hardware.

SUMMARY

According to an aspect of the embodiments, a blood flow index calculating method includes: obtaining, by a camera, an image capturing a first site of a living body and a second site of the living body, the first site being a part of the living body of a subject, and the second site being a site different from the first site; extracting an area of the first site of the living body and an area of the second site of the living body, the areas being included in the image, by a processor; detecting a pulse wave pattern of the first site of the living body from the area of the first site of the living body and detecting a pulse wave pattern of the second site of the living body from the area of the second site of the living body, by the processor; first calculating a delay amount from the pulse wave pattern of the first site of the living body and the pulse wave pattern of the second site of the living body, by the processor; and second calculating an index related to blood flow by using the delay amount, by the processor.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Hereinafter, a blood flow index calculating method, a blood flow index calculating program, and a blood flow index calculating apparatus according to the present application will be described with reference to the appended drawings. Their embodiments do not limit the disclosed techniques. The embodiments may be combined with one another as appropriate, so long as no contradiction arises in the contents processed.

First Embodiment

[Configuration of Blood Flow Index Calculating Apparatus]

Figure 1:
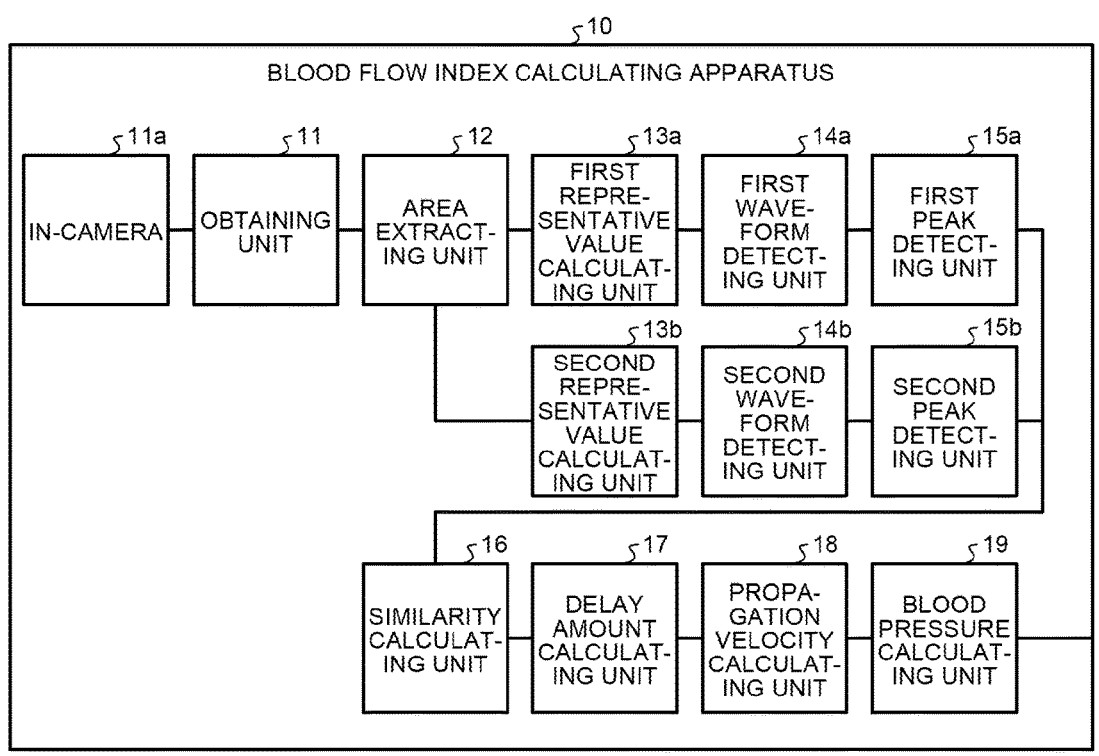
FIG. 1 is a block diagram illustrating a functional configuration of a blood flow index calculating apparatus according to a first embodiment.

First of all, a functional configuration of a blood flow index calculating apparatus according to an embodiment will be described. FIG. 1 is a block diagram illustrating a functional configuration of a blood flow index calculating apparatus according to a first embodiment. A blood flow index calculating apparatus 10 illustrated in FIG. 1 detects pulse waves of a subject, that is, variation in volume of blood associated with beating of the heart, without causing a measuring device to come into contact with the subject under general ambient light, such as sunlight or indoor light. In particular, the blood flow index calculating apparatus 10 executes a blood flow index calculating process of detecting pulse waves of two sites of a living body from an image simultaneously capturing plural sites of the living body, that is, variation in volume of blood associated with beating of the heart, and calculating an index related to blood flow from a delay amount, which is a time difference between two pulse wave patterns.

In one aspect, the blood flow index calculating apparatus 10 may be implemented by a blood flow index calculating program being installed on a desired computer, the blood flow index calculating program being provided as packaged software or online software. For example, the blood flow index calculating program is installed on a mobile communication terminal, such as a mobile phone or a personal handyphone system (PHS), which is connectable to a mobile communication network. Further, not being limited to the mobile communication terminal connectable to the mobile communication network, the blood flow index calculating program may be installed on a digital camera or a tablet terminal, which does not have the ability to connect to a mobile communication network. Thereby, the portable terminal, such as the mobile communication terminal or the tablet terminal, is able to be caused to function as the blood flow index calculating apparatus 10. The portable terminal has been described as an implementation example of the blood flow index calculating apparatus 10, but the blood flow index calculating program may be installed on a stand alone type terminal device including a personal computer.

As illustrated in FIG. 1, the blood flow index calculating apparatus 10 has an in-camera 11a, an obtaining unit 11, an area extracting unit 12, a first representative value calculating unit 13a, a second representative value calculating unit 13b, a first waveform detecting unit 14a, and a second waveform detecting unit 14b. Further, the blood flow index calculating apparatus 10 has a first peak detecting unit 15a, a second peak detecting unit 15b, a similarity calculating unit 16, a delay amount calculating unit 17, a propagation velocity calculating unit 18, and a blood pressure calculating unit 19.

The blood flow index calculating apparatus 10 may have various functional units that a known computer has, other than the functional units illustrated in FIG. 1. For example, if the blood flow index calculating apparatus 10 is implemented as a stand alone terminal, the blood flow index calculating apparatus 10 may further have input and output devices, such as a keyboard, a mouse, and a display. Further, if the blood flow index calculating apparatus 10 is implemented as a tablet terminal or a slate terminal, the blood flow index calculating apparatus 10 may further have an acceleration sensor or an angular velocity sensor. Furthermore, if the blood flow index calculating apparatus 10 is implemented as a mobile communication terminal, the blood flow index calculating apparatus 10 may further have functional units, such as an antenna, a wireless communication unit that connects to a mobile communication network, a global positioning system (GPS) receiver, and the like.

The in-camera 11a is an imaging device, in which an imaging element, such as a charge coupled device (CCD) or a complementary metal oxide semiconductor (CMOS), is installed. For example, light receiving elements of three or more types, such as red (R), green (G), and blue (B), may be installed. Although the case where the in-camera 11a is used has been described as an example, any camera installed in a portable terminal or the like may be used, and the camera is not necessarily arranged on the same side as a surface on which a screen is arranged.

The in-camera 11a is a camera installed on a side where a liquid crystal display screen not illustrated is present, and a subject who uses the portable terminal is able to cause an image of the subject to be projected on the liquid crystal display by the in-camera 11a and to perform shooting while checking how the image is taken. The in-camera 11a may be arranged at any position, as long as the in-camera 11a is on the same side as the surface on which the screen is arranged.

When the above described blood flow index calculating program is activated, the in-camera 11a keeps different sites of a living body in an imaging range that the in-camera 11a has, and simultaneously captures an image of the plural sites of the living body. As an example, the following description will be made supposing a case where the face of a subject is shot as a first site of a living body and the hand of the subject is shot as a second site of the living body, by the in-camera 11a.

Figure 2:
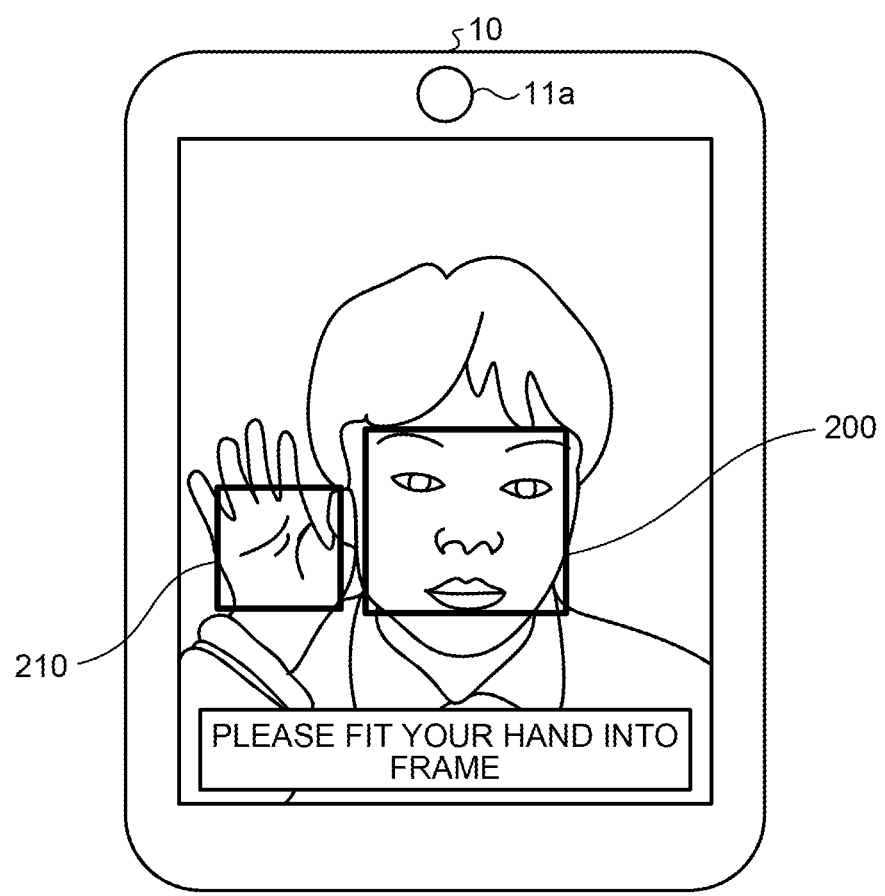
FIG. 2 is a diagram illustrating an example of a shooting method.

FIG. 2 is a diagram illustrating an example of a shooting method. As illustrated in FIG. 2, the in-camera 11a keeps the screen side of the liquid crystal display of the blood flow index calculating apparatus 10 in the imaging range and captures an image of a subject present in the imaging range. When that is done, on the liquid crystal display of the blood flow index calculating apparatus 10, aim of a shooting position of the face may be displayed as a face guide 200 while an image to be shot by the in-camera 11a is being displayed. Thereby, the subject is able to move the face of the subject or the blood flow index calculating apparatus 10 such that the face of the subject fits in the face guide 200 with the face guide 200 being the aim, and thus shooting is able to be performed in a state where the face of the subject is fitted in the imaging range of the in-camera 11a.

As described above, the face guide 200 may be displayed on the liquid crystal display and aim of a shooting position of the hand may be displayed as a hand guide 210. Thereby, the subject is able to move the hand of the subject or the blood flow index calculating apparatus 10 such that the hand of the subject fits in the hand guide 210, with the hand guide 210 being the aim, and thus shooting is able to be performed in a state where the hand of the subject is fitted in the imaging range of the in-camera 11a. In the hand guide 210, either the left or right hand of the subject may be fitted, and either the palm of the hand or the back of the hand may be fitted.

Further, by execution of image processing, such as skin color detection, on an image in the hand guide 210, whether or not the hand of the subject is in the hand guide 210 may be detected. If the hand of the subject is not in the hand guide 210, a message, such as "Please fit your hand into the frame", may be displayed on the liquid crystal display, or the message may be output as voice from a speaker.

By guidance of these face guide 200 and hand guide 210, the face and hand of the subject are able to be fitted to predetermined positions in the imaging range of the in-camera 11a and the face and hand of the subject are able to be shot simultaneously by the in-camera 11a. Further, since the hand guide 210 is displayed side by side with the face guide 200, shooting is executed in a state where the subject has raised the hand of the subject to the same height as the face of the subject, with the hand guide 210 being the aim. Therefore, an image shot with the face and hand of the subject being approximately at the same height is also able to be obtained.

The image captured by the in-camera 11a as described above is output to the later described obtaining unit 11. Hereinafter, the image captured by the in-camera 11a may be referred to as "original image". Although the case where the original image is output to the obtaining unit 11 after the imaging has been described, the original image is not necessarily output immediately to the obtaining unit 11. For example, the original image may be temporarily stored in an auxiliary storage device, such as a flash memory or a hard disk, or a removable medium, such as a memory card, which is not illustrated.

The obtaining unit 11 is a processing unit that obtains an image. In one aspect, the obtaining unit 11 obtains the original image captured by the in-camera 11a. In another aspect, the obtaining unit 11 may obtain an image from an auxiliary storage device, such as a hard disk or an optical disk, in which original images are accumulated, or a removable medium, such as a memory card or a universal serial bus (USB) memory. In yet another aspect, the obtaining unit 11 may obtain the original image by receiving the original image via a network from an external device. Although the case, in which the obtaining unit 11 executes processing by using image data, such as two-dimensional bitmap data or vector data, obtained from output by the imaging element, such as the CCD or CMOS, has been described, the obtaining unit 11 may cause later stage processing to be executed by directly obtaining a signal output from one detector.

The area extracting unit 12 is a processing unit that extracts areas of the first site of the living body and the second site of the living body from the image obtained by the obtaining unit 11. In one aspect, the area extracting unit 12 extracts a face area based on a predetermined face part from the original image. For example, the area extracting unit 12 detects a particular face part, of the so-called face parts, which are organs of the face, such as the eye, ear, nose, and mouth of the subject, that is, the nose of the subject, by executing image processing, such as template matching, on the original image. In addition, the area extracting unit 12 extracts a face area included in a predetermined range from a center, with the nose of the subject being the center. Thereby, an image of a face area including the nose of the subject and a face center portion of a part of the cheek positioned around the nose, is extracted as an image to be used in detection of pulse waves. Thereafter, the area extracting unit 12 outputs the image of the face area extracted from the original image to the first waveform detecting unit 14a.

Figure 3:
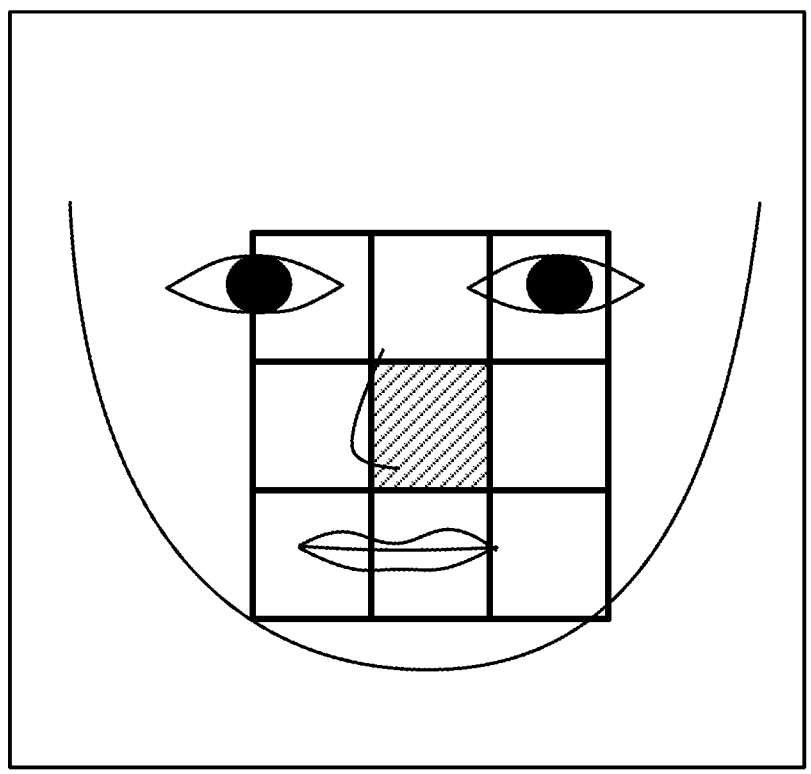
FIG. 3 is a diagram illustrating an example of an original image.

FIG. 2 is a diagram illustrating an example of the original image. In FIG. 3, an area, in which the face of the subject is projected, is illustrated with the area having been cut out from the original image, and blocks, which result from division of an area including a part or all of the eyes, nose, and mouth of the subject into nine, are illustrated. In the top left and right blocks of the blocks illustrated in FIG. 3, the eyes of the subject are taken. If images of these blocks are used in detection, accuracy of detection of pulse waves may be reduced as blinking of the eyes becomes noise. Further, in the bottom three blocks of the blocks illustrated in FIG. 3, the mouth of the subject is taken. If images of these blocks are used in the detection, accuracy of the detection of pulse waves may be reduced as movement of the mouth becomes noise. On the contrary, the center block in the middle illustrated in FIG. 3, that is, the block illustrated with oblique lined shading, is separated from the blocks in which the eyes or the mouth are/is taken, and the possibility that components that become the noise are taken in that block is low as compared with the other blocks, and thus satisfactory detection results are able to be expected. Therefore, the area extracting unit 12 extracts, as an image of an area of the living body, an image of the center block in the middle illustrated in FIG. 3 from the original image.

Concurrently with the extraction of the face area, the area extracting unit 12 extracts a hand area from the original image. For example, the area extracting unit 12 extracts, as the hand area, an area having a skin color and a shape of the hand, from the original image, by executing skin color detection and pattern matching on the original image. The area extracting unit 12 may utilize the result of the extraction of the face area in the extraction of the hand area. For example, if the area extracting unit 12 executes the skin color detection and pattern matching, the part extracted as the face area may be excluded from a target to be extracted, to extract the hand area.

In another aspect, the area extracting unit 12 may extract, as the image of the face area, a partial image of an area corresponding to the face guide 200 illustrated in FIG. 2, and extract, as the image of the hand area, a partial image of an area corresponding to the hand guide 210 illustrated in FIG. 2. As described above, when the extraction of the face area and hand area is executed by use of the face guide 200 and hand guide 210, image processing, such as the skin color detection and template matching, is not necessarily performed, such that the processing load is reduced. Although, the partial image of each guide has been described as being cut out as it is, the skin color detection and the face guide 200 and hand guide 210 may be used together. For example, the face guide 200 and hand guide 210 may be utilized only when a skin color area having a predetermined area or larger is detected from both the partial image of the area corresponding to the face guide 200 and the partial image of the area corresponding to the hand guide 210.

The first representative value calculating unit 13a is a processing unit that calculates a representative value of pixel values that respective pixels included in an area of the first site of the living body have. In one aspect, the first representative value calculating unit 13a averages pixel values that pixels included in the face area have, for each wavelength component. Furthermore, other than the average value, the median or the mode may be calculated, and other than weighted averaging, any averaging processing, such as, for example, weighted averaging or moving averaging, may be executed. Thereby, the average value of the pixel values that the respective pixels included in the face area have is calculated as the representative value representing the face area, for each wavelength component. Although the representative value of the pixel values of each wavelength component has been described to be calculated, in the later described first waveform detecting unit 14a, since pixel values of the R-component and G-component of the three components of RGB are used, representative values of these two components may be calculated.

The second representative value calculating unit 13b is a processing unit that calculates a representative value of pixel values that respective pixels included in an area of the second site of the living body have. In one aspect, the second representative value calculating unit 13b averages pixel values that pixels included in the hand area have, for each wavelength component. Thereby, the average value of the pixel values that the respective pixels included in the hand area have is calculated as the representative value representing the hand area for each wavelength component. Although the representative value of the pixel values of each wavelength component has been described to be calculated, in the later described second waveform detecting unit 14b, since pixel values of the G-component of the three components of RGB are used, a representative value of the G-component may be calculated.

The first waveform detecting unit 14a is a processing unit that detects a pattern of a pulse wave signal of the first site of the living body from a signal of the representative value for each wavelength component of the respective pixels included in the area of the first site of the living body. In one aspect, the first waveform detecting unit 14a detects a pattern of a pulse wave signal in which components of a particular frequency band other than a pulse wave frequency band that pulse waves are possibly in are offset by one another among the respective wavelength components, from a signal of the representative value for each wavelength component in the face area, by executing a first waveform detecting process described below. For example, the first waveform detecting unit 14a detects a waveform, by using time series data of representative values of the two wavelength components, the R-component and G-component, having different light absorption characteristics in blood, of the three wavelength components, that is, the R-component, G-component, and B-component.

Specifically, capillary blood vessels flow through a surface of the face, and when blood flow flowing through a blood vessel changes due to the heartbeat, amount of light absorbed by the blood flow also change according to the heartbeat and thus luminance obtained by reflection from the face also changes in association with the heartbeat. The amount of change in luminance is small, but if an average luminance of the whole face area is found, a pulse wave component is included in time series data of the luminance. However, the luminance changes due to, other than the pulse waves, the body motion or the like, and this becomes a noise component of pulse wave detection, which is the so-called body motion artifact. Thus, pulse waves are detected with two type of wavelength with different light absorption characteristics in the blood, for example, the G-component (about 525 nm) having a high absorption property and the R-component (about 700 nm) having a low light absorption property. Since the heartbeat is 0.5 Hz to 4 Hz, which is in a range of 30 bpm to 240 bpm when converted into values per minute, the other components are able to be regarded as noise components. If it is assumed that the noise has no wavelength characteristics, or even if the noise has any wavelength characteristics, the wavelength characteristics are minute, components other than those of 0.5 Hz to 4 Hz are supposed to be equal to each other between the G-signal and the R-signal, but due to a sensitivity difference in the camera, their magnitudes differ from each other. Therefore, by correcting the sensitivity difference of the components other than those of 0.5 Hz to 4 Hz and subtracting the R-component from the G-component, the noise components will be removed and only pulse wave components will be able to be taken out.

For example, the G-component and R-component are able to be expressed by the following Equation (1) and Equation (2). In the following Equation (1), "Gs" refers to a pulse wave component of the G-signal, "Gn" refers to a noise component of the G-signal, and in the following Equation (2), "Rs" refers to a pulse wave component of the R-signal and "Rn" refers to a noise component of the R-signal. Further, since the noise components have a sensitivity difference between the G-component and R-component, a correction coefficient k of the sensitivity difference is expressed by the following Equation (3).

$$Ga=Gs+Gn \quad (1)$$

$$Ra=Rs+Rn \quad (2)$$

$$k=Gn/Rn \quad (3)$$

When the sensitivity difference is corrected and the R-component is subtracted from the G-component, a pulse wave component "S" is expressed by the following Equation (4). When this is modified into an equation expressed by Gs, Gn, Rs, and Rn by use of the above Equation (1) and the above Equation (2), the following Equation (5) is obtained, and further, the following Equation (6) is derived by use of the above Equation (3), deletion of k, and rearrangement of the equation.

$$S=Ga-kRa \quad (4)$$

$$S=Gs+Gn-k(Rs+Rn) \quad (5)$$

$$S=Gs-(Gn/Rn)Rs \quad (6)$$

Light absorption characteristics of the G-signal and R-signal are different from each other, and Gs>(Gn/Rn)Rs. Therefore, a pulse wave component S, from which the noise has been removed by the above Equation (6), is able to be calculated.

Figure 4:
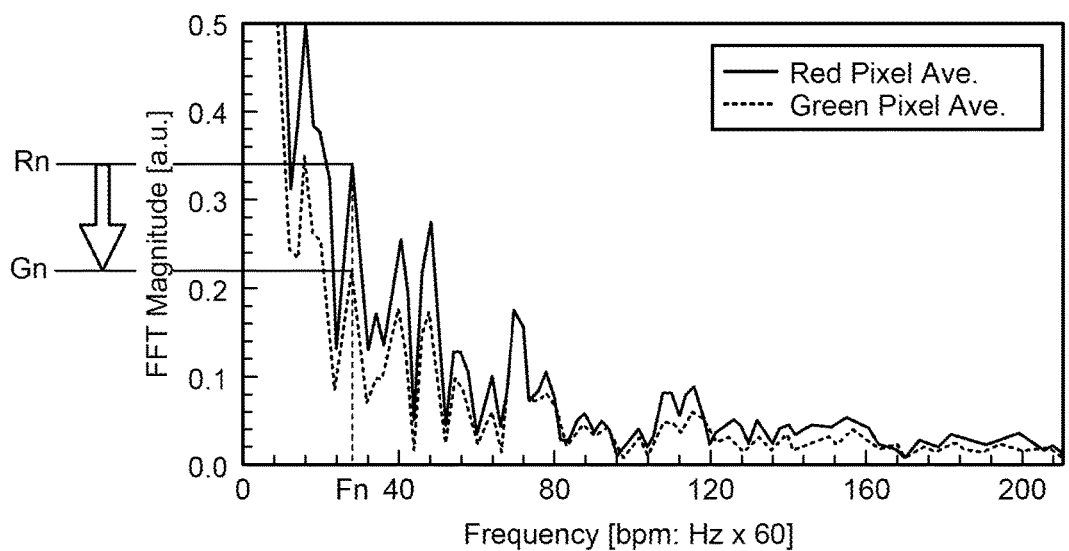
FIG. 4 is a diagram illustrating an example of each signal spectrum of a G-signal and an R-signal.

FIG. 4 is a diagram illustrating an example of each signal spectrum of the G-signal and R-signal. The vertical axis of the graph illustrated in FIG. 4 indicates signal strength, and the horizontal axis indicates frequency (bpm). As illustrated in FIG. 4, since the sensitivities of the imaging element for the G-component and R-component differ from each other, they have different signal strengths from each other. For both the R-component and G-component, noise appears outside a range of 30 bpm to 240 bpm, in particular, in a particular frequency band of equal to or greater than 3 bpm and less than 20 bpm. Therefore, as illustrated in FIG. 4, the signal strengths corresponding to a specified frequency Fn included in the particular frequency band of equal to or greater than 3 bpm and less than 20 bpm are able to be extracted as the Gn and Rn. The correction coefficient k of the sensitivity difference is able to be derived from these Gn and Rn.

Figure 5:
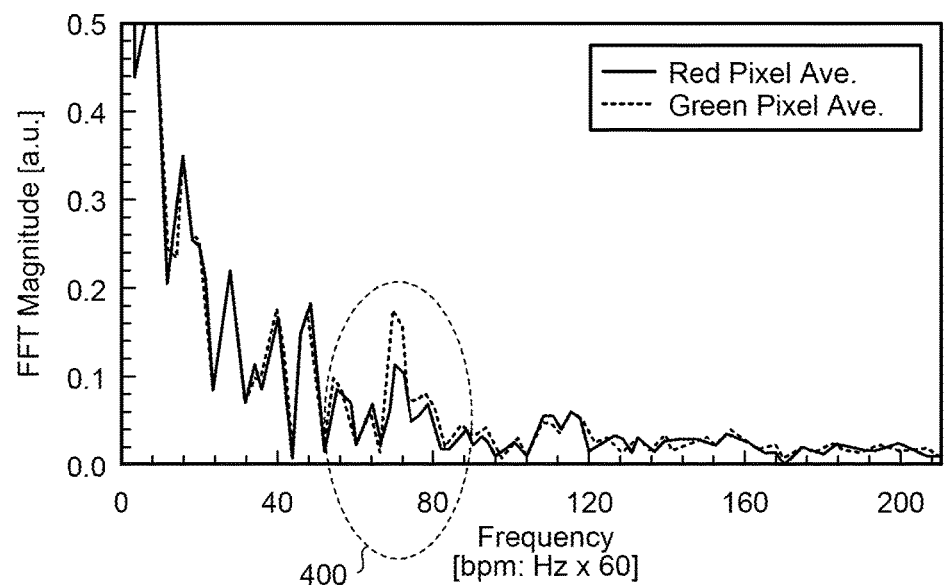
FIG. 5 is a diagram illustrating an example of a spectrum of each signal of a G-component and an R-component multiplied by a correction coefficient k.

FIG. 5 is a diagram illustrating an example of a spectrum of each signal of the G-component, and the R-component that has been multiplied by the correction coefficient k. In the example of FIG. 5, for convenience of explanation, a result obtained by multiplication by an absolute value of the correction coefficient is illustrated. In the graph illustrated in FIG. 5 also, the vertical axis indicates signal strength, and the horizontal axis indicates frequency (bpm). As illustrated in FIG. 5, when the spectrum of each signal of the G-component and R-component is multiplied by the correction coefficient k, the sensitivities become equal to each other between the G-component and R-component. In particular, the signal strengths of the spectra in most of the particular frequency band are approximately the same. On the contrary, in a peripheral area 400 around the frequency actually including the pulse waves, the signal strengths of the spectra are not equal to each other between the G-component and R-component.

Figure 6:
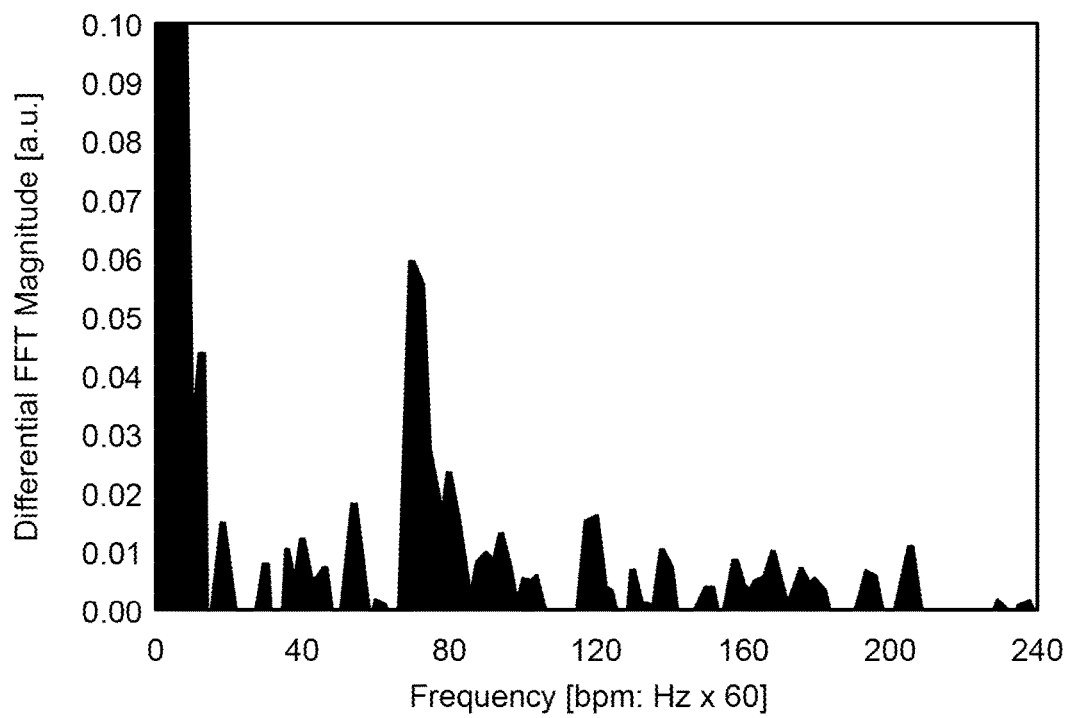
FIG. 6 is a diagram illustrating an example of a spectrum after computation.

FIG. 6 is a diagram illustrating an example of a spectrum after computation. In FIG. 6, the scale of the signal strength on the vertical axis is largely illustrated in order to increase visibility of the frequency band in which the pulse waves appear. As illustrated in FIG. 6, it is understood that when the spectrum of the R-signal that has been multiplied by the correction coefficient k is subtracted from the G-signal, the noise component is reduced in a state, in which the strength of the signal component where the pulse waves appear due to the difference in the light absorption characteristics between the G-component and R-component is maintained as much as possible. As described above, a waveform of the pulse wave signal, from which only the noise component has been removed, is able to be detected.

Figure 7:
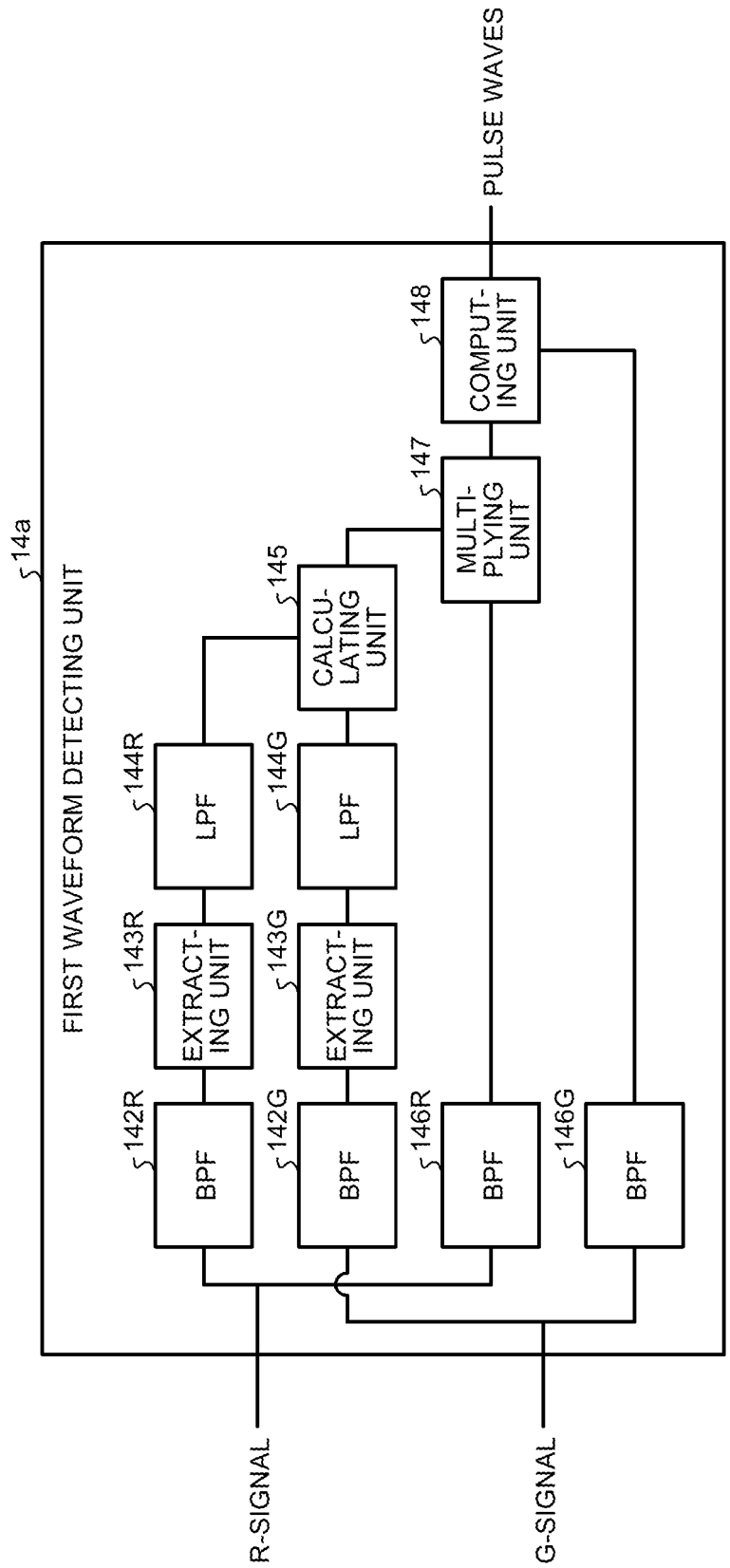
FIG. 7 is a block diagram illustrating a functional configuration of a first waveform detecting unit illustrated in FIG. 1.

Subsequently, a functional configuration of the first waveform detecting unit 14*a* will be more specifically described. FIG. 7 is a block diagram illustrating the functional configuration of the first waveform detecting unit 14*a* illustrated in FIG. 1. As illustrated in FIG. 7, the first waveform detecting unit 14*a* has band-pass filters (BPFs) 142R and 142G, extracting units 143R and 143G, low-pass filters (LPFs) 144R and 144G, a calculating unit 145, BPFs 146R and 146G, a multiplying unit 147, and a computing unit 148. In the examples of FIG. 4 to FIG. 6, the example in which the pulse waves are detected in a frequency space has been described, but in FIG. 7, from the viewpoint of reducing the time taken for the conversion to frequency components, a functional configuration for a case where pulse waves are detected by canceling a noise component in a time-series space is illustrated.

For example, from the area extracting unit 12 to the first waveform detecting unit 14*a*, time series data of the R-signal are input, the R-signal having, as a signal value, a representative value of pixel values of the R-component that respective pixels included in the face area have, and time series data of the G-signal are input, the G-signal having, as a signal value, a representative value of G-component pixel values that respective pixels included in the face area have. Of these, the R-signal of the face area is input to the BPF 142R and BPF146R in the first waveform detecting unit 14*a*, and the G-signal of the face area is input to the BPF 142G and BPF 146G of the first waveform detecting unit 14*a*.

Each of the BPF 142R, BPF 142G, BPF 146R, and BPF 146G is a band-pass filter that passes only a signal component of a predetermined frequency band and removes signal components of a frequency band other than the predetermined frequency band. These BPF 142R, BPF 142G, BPF 146R, and BPF 146G may be implemented by hardware, or implemented by software.

Differences among the frequency bands that these BPFs pass will be described. The BPF 142R and BPF 142G pass a signal component of a particular frequency band where a noise component appears more prominently than in the other frequency band.

That particular frequency band may be determined by comparison with a frequency band that the pulse waves are possibly in. An example of the frequency band that the pulse waves are possibly in is a frequency band of equal to or greater than 0.5 Hz and equal to or less than 4 Hz, which is a frequency band equal to or greater than 30 bpm and equal to or less than 240 bpm if converted into values per minute. Therefore, as an example of the particular frequency band, frequency bands less than 0.5 Hz and greater than 4 Hz, which are not possibly measured as the pulse waves, may be adopted. Further, a part of the particular frequency band may overlap the frequency band that the pulse waves are possibly in. For example, by allowing the overlap with the frequency band that the pulse waves are possibly in within an interval of 0.7 Hz to 1 Hz, which the pulse waves are difficult to be supposed to have, frequency bands less than 1 Hz and greater than 4 Hz may be adopted as the particular frequency band. Further, the particular frequency band may be narrowed down to a frequency band, which has frequency bands less than 1 Hz and equal to or greater than 4 Hz as outer edges and in which the noise appears more prominently. For example, the noise appears more prominently in a low frequency band, which is lower than the frequency band that the pulse wave are possibly in, than in a high frequency band, which is higher than the frequency band that the pulse waves are possibly in. Therefore, the particular frequency band may be narrowed down to a frequency band of less than 1 Hz. Further, near a direct current component having a spatial frequency of zero, a large sensitivity difference between the imaging elements for the respective components is included, and thus, the particular frequency band may be narrowed down to a frequency band of equal to or greater than 0.05 Hz and less than 1 Hz. Furthermore, the particular frequency band may be narrowed down to a frequency band of equal to or greater than 0.05 Hz and equal to or less than 0.3 Hz, where noises, such as, in addition to movement of the body of a human, for example, blinking or shaking of the body, flickering of ambient light, are likely to appear.

As one example, the following description will be made supposing a case where the BPF 142R and BPF 142G pass any signal component of a frequency band of equal to or greater than 0.05 Hz and equal to or less than 0.3 Hz, as the particular frequency band. Although the case where the band-pass filters are used in order to extract the signal components of the particular frequency band has been described as an example, in a case where signal components of a frequency band less than a certain frequency are extracted, or the like, low-pass filters may be used.

The BPF 146R and BPF 146G pass any signal component of the frequency band that the pulse waves are possibly in, for example, a frequency band of equal to or greater than 0.5 Hz and equal to or less than 4 Hz. Hereinafter, the frequency band that the pulse waves are possibly in may be referred to as "pulse wave frequency band".

The extracting unit 143R extracts an absolute value of a strength of a signal component of the particular frequency band of the R-signal. For example, the extracting unit 143R extracts an absolute value of a strength of a signal component of the particular frequency band by executing an absolute value computing process on the signal component of the particular frequency band of the R-component. Further, the extracting unit 143G extracts an absolute value of a strength of a signal component of the particular frequency band of the G-signal. For example, the extracting unit 143G extracts an absolute value of a strength of a signal component of the particular frequency band by executing the absolute value computing process on the signal component of the particular frequency band of the G-component.

The LPF 144R and LPF 144G are low-pass filters that execute a smoothing process of causing time series data of absolute values of strengths of the particular frequency band to respond to time change. These LPF 144R and LPF 144G differ from each other only in that a signal input to the LPF 144R is the R-signal, and a signal input to the LPF 144G is the G-signal. By the smoothing process, the absolute values of the strengths of the particular frequency band, R'n and G'n, are able to be obtained.

The calculating unit 145 executes division, "G'n/R'n", of dividing the absolute value of the strength G'n of the particular frequency band of the G-signal output by the LPF 144G, by the absolute value of the strength R'n of the particular frequency band of the R-signal output by the LPF 144R. Thereby, the correction coefficient k of the sensitivity difference is calculated.

The multiplying unit 147 multiplies the signal component of the pulse wave frequency band of the R-signal output by the BPF 146R by the correction coefficient k calculated by the calculating unit 145.

The computing unit 148 executes computation, "Gs−k*Rs", of subtracting the signal component of the pulse wave frequency band of the R-signal that has been multiplied by the correction coefficient k by the multiplying unit 147, from the signal component of the pulse wave frequency band of the G-signal output by the BPF 146G. The time series data of the signals obtained as described above correspond to a waveform of a pulse wave signal of the face, and the sampling frequency thereof corresponds to the frame frequency at which the images are captured. Hereinafter, the waveform of the pulse wave signal may be referred to as "pulse wave pattern".

Returning to the description of FIG. 1, the second waveform detecting unit 14b is a processing unit that detects, from a signal of a representative value of pixels included in an area of the second site of the living body, a waveform of a pulse wave signal, from which any component of the particular frequency band other than the pulse wave frequency band has been removed. In one aspect, the second waveform detecting unit 14b uses the representative value of the G-component, of the representative values for the different wavelength components of the hand area calculated by the second representative value calculating unit 13b, in detection of the pulse waves of the hand. That is, the second waveform detecting unit 14b removes any signal component of the particular frequency band included in the signal of the representative value of the G-component in the hand area and causes the signal component of the pulse wave frequency band to pass, by use of a BPF or the like, which is not illustrated. Thereby, the signal component of the pulse wave frequency band is extracted. The time series data of the signals of the pulse wave frequency band output by the second waveform detecting unit 14b correspond to the pulse wave pattern of the hand. The second waveform detecting unit 14b may detect the pulse wave pattern of the hand from the representative value of the G-component and the representative value of the R-component, similarly to the above described first waveform detecting unit 14a.

The first peak detecting unit 15a is a processing unit that detects a peak of the pulse wave pattern of the first site of the living body. In one aspect, the first peak detecting unit 15a calculates a differential waveform of the pulse waves of the face by time differentiating the pulse wave pattern of the face detected by the first waveform detecting unit 14a and detects a zero cross point at which the sign of the differential coefficient changes from positive to negative, that is, a maximum point indicating a peak. For example, every time an amplitude value of the pulse wave pattern of the face is detected, the first peak detecting unit 15a determines whether or not the differential coefficient of the amplitude value detected at the sampling point that is the one before the current detection is zero. If the differential coefficient of the amplitude value detected at the sampling point that is the one before the current detection is zero, the first peak calculating unit 15a further determines whether or not the signs of the differential coefficients of the amplitude values at sampling points before and after the sampling point change from positive to negative. As a result, if the signs of the differential coefficients change from positive to negative before and after the sampling point, the first peak calculating unit 15a detects the sampling point at which the differential coefficient is zero as a peak of the pulse wave pattern of the face and registers the time of the sampling point, at which the peak appears, into an internal memory not illustrated. The detection of a peak is not necessarily realized by time differentiation of the pulse wave pattern, and may be detected from the pulse wave pattern itself of the face.

The second peak detecting unit 15b is a processing unit that detects a peak of the pulse wave pattern of the second site of the living body. In one aspect, similarly to the above described first peak detecting unit 15a, the second peak detecting unit 15b detects a peak of the pulse wave pattern of the hand by detecting a zero cross point from a differential waveform of the pulse waves of the hand detected by the second waveform detecting unit 14b, and registers the time of the sampling point, at which the peak appears, into the internal memory.

Figure 8:
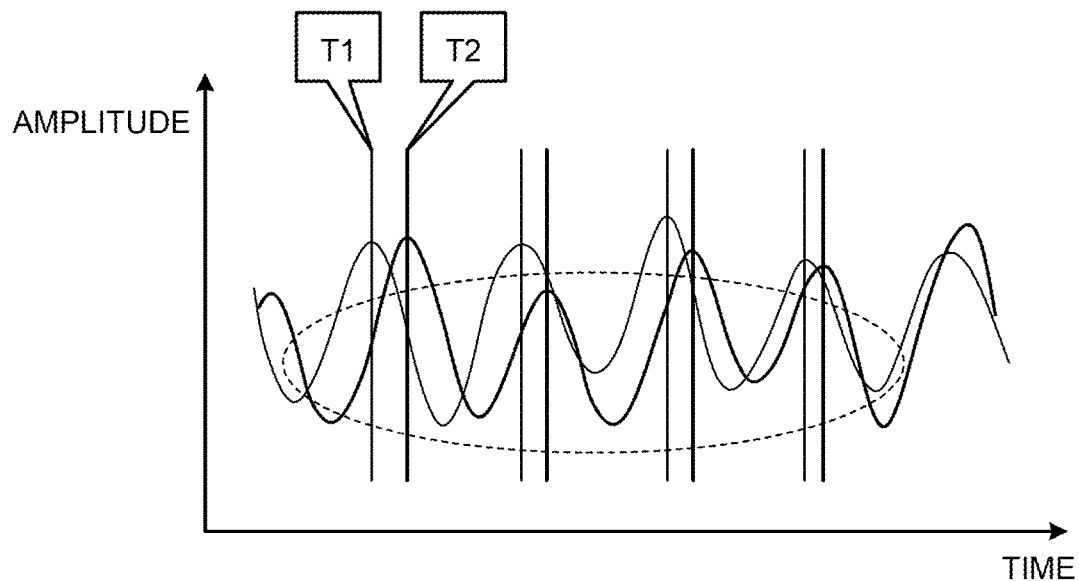
FIG. 8 is a diagram illustrating an example of pulse waves of a face and pulse waves of a hand.

FIG. 8 is a diagram illustrating an example of the pulse waves of the face and the pulse waves of the hand. The vertical axis of the graph illustrated in FIG. 8 indicates signal strength (amplitude), and the horizontal axis indicates time. As illustrated in FIG. 8, while a peak appears at a time point, T1, in the pulse waves of the face, a peak appears at a time point, T2, in the pulse waves of the hand. It is understood that the time points at which the peaks appear are different from each other between these pulse waves of the face and pulse waves of the hand, and the peak of the pulse waves of the hand is later than the peak of the pulse waves of the face. This is because there are time differences among timings at which the blood sent out from the heart reaches respective sites of the living body. In general, since the hand is more away from the heart than the face, the pulse waves propagate to the hand after propagating to the face first.

The similarity calculating unit 16 is a processing unit that calculates a similarity between the pulse wave pattern of the first site of the living body and the pulse wave pattern of the second site of the living body. In one aspect, the similarity calculating unit 16 calculates, as a similarity, a difference between a cycle of peaks obtained from the pulse wave pattern of the face and a cycle of peaks obtained from the pulse wave pattern of the hand. For example, the similarity calculating unit 16 executes the following process, when a period over which detection of peaks from the pulse wave pattern of the face and pulse wave pattern of the hand by the first peak detecting unit 15a and second peak detecting unit 15b has gone over a predetermined peak measurement period, for example, five seconds. That is, the similarity calculating unit 16 calculates an average value of cycles of peaks between respective peaks included in the pulse wave pattern of the face and calculates an average value of cycles of peaks between respective peaks included in the pulse wave pattern of the hand. For example, the similarity calculating unit 16 may calculate, by using the following Equation (7), average values of cycles of peaks in the pulse wave pattern of the face and pulse wave pattern of the hand when the sampling time over which the peaks have been detected is $T_n$. In addition, the similarity calculating unit 16 calculates a difference between the average values of the cycles of the peaks of the pulse wave pattern of the face and pulse wave pattern of the hand.

$$\frac{1}{n}\sum_{k=0}^{n}(T_{k+1} - T_k) \qquad (7)$$

The smaller the difference between the average values of the cycles of the peaks is, the more similar the pulse wave pattern of the face and the pulse wave pattern of the hand are to each other. This is based on the fact that the pulse waves of the same person are approximately the same even if the sites at which the pulse waves are measured are different. That is, the smaller the difference between the average values of the cycles of the peaks is, the higher the possibility that both the pulse wave pattern of the face and the pulse wave pattern of the hand have been measured becomes.

In another aspect, the similarity calculating unit 16 uses a cross correlation function in the above described calculation of the similarity. For example, if the sampling time of the pulse wave signals of the face and hand is "t", the amplitude value of the pulse wave pattern of the face is "X(t)", the amplitude value of the pulse wave pattern of the hand is "Y(t)", and the delay amount is "τ", the similarity $C_{XY}(\tau)$ is able to be derived by the following Equation (8). If a cross correlation function is used as described above, the higher the similarity $C_{XY}(\tau)$ is, the more similar the pulse wave pattern of the hand shifted by the delay amount τ is to the pulse wave pattern of the face. The τ at which the similarity $C_{XY}(\tau)$ calculated as described above takes the maximum similarity may be used as a delay amount between the pulse wave pattern of the face and pulse wave pattern of the hand.

$$C_{XY}(\tau) = \Sigma X(t)Y(t+\tau) \qquad (8)$$

The delay amount calculating unit 17 is a processing unit that calculates a delay amount between the pulse wave pattern of the first site of the living body and the pulse wave pattern of the second site of the living body. The delay amount calculating unit 17 does not necessarily calculate a delay amount immediately just because the pulse wave pattern of the face and the pulse wave pattern of the hand are detected. That is, the delay amount calculating unit 17 executes calculation of a delay amount targeting a case in which the similarity calculated by the similarity calculating unit 16 is equal to or greater than a predetermined threshold. For example, the delay amount calculating unit 17 determines whether or not the similarity is equal to or less than the predetermined threshold when the difference between the average values of the cycles of the peaks is calculated as the similarity. The delay amount calculating unit 17 executes calculation of the delay amount if the similarity is equal to or less than the threshold. Further, if the similarity is calculated by a cross correlation function and the similarity is equal to or greater than a predetermined threshold, the delay amount calculating unit 17 executes calculation of a delay amount. Thereby, calculation of a delay amount is able to be executed targeting a case in which the possibility that the pulse wave pattern of the face and pulse wave pattern of the hand have been able to be measured is high.

In one aspect, the delay amount calculating unit 17 calculates a delay amount between the pulse waves of the face and hand by calculating a time difference between the time of the peak detected from the pulse wave pattern of the face by the first peak detecting unit 15a and the time of the peak detected from the pulse wave pattern of the hand by the second peak detecting unit 15b. When this is done, the delay amount calculating unit 17 may calculate a delay amount by using plural pairs of peaks of the pulse wave pattern of the face and peaks of the pulse wave pattern of the hand. For example, a predetermined number of the pairs of the peaks of the pulse wave pattern of the face and the peaks of the pulse wave pattern of the hand detected in a peak measurement period may be extracted in order from the newest one, and an average time difference calculated among the respective pairs may be calculated as a delay amount. If a cross correlation function is used in the calculation of the similarity, the τ at which the similarity is maximum may be directly adopted as the delay amount.

For example, in the example illustrated in FIG. 8, the delay amount calculating unit 17 may calculate a delay amount between the hand and face by subtracting a time T1 from a time T2. Although in this example, the time T1, at which a peak is detected in the pulse wave pattern of the face, is subtracted from the time T2, at which a peak is detected in the pulse wave pattern of the hand, but T2 may be subtracted from T1, and in that case, by taking an absolute value, the same value is able to be calculated.

The propagation velocity calculating unit 18 is a processing unit that calculates a pulse wave velocity by using the delay amount between the first site of the living body and the second site of the living body. Distance and time are used in calculation of the velocity, and with respect to the time, of the distance and time, the delay amount, which is a time difference between propagation of pulse waves to the face and propagation of the pulse waves to the hand, is found by the delay amount calculating unit 17. Thus, by calibrating, in advance, a distance difference between a distance from the heart, which is the starting point of the pulse waves, to the finger and a distance from the heart to the face, with use of the following Equation (9), the pulse wave velocity is able to be calculated. In this Equation (9), "Vp" indicates the pulse wave velocity, "L" indicates the distance difference between the distance from the heart to the finger and the distance from the heart to the face, and "Td" indicates the delay amount.

$$Vp = L/Td \qquad (9)$$

That is, the propagation velocity calculating unit 18 is able to calculate a pulse wave velocity Vp by substituting the delay amount Td calculated by the delay amount calculating unit 17 and the distance difference L set on the internal memory, into the above Equation (9). This distance difference L may be initially set by a user of the blood flow index calculating apparatus 10, for example. For example, via an input device not illustrated, the user may be caused to input a value itself of the distance difference L, or the user may perform the initial setting by being caused to input a distance L1 from the heart to the face and a distance L2 from the heart to the finger. Further, a distance difference may be initially set by age, sex, and height caused to be input by the user being searched from statistical data associating statistics of distance differences, which correspond to combinations of items, such as age, sex, and height, respectively with the combinations.

The above described pulse wave velocity is a useful index for diagnosing progress of arteriosclerosis, and for example, vascular age or the like is able to be measured from the propagation velocity. As described above, by being output to an application program for calculating progress of arteriosclerosis and vascular age, the pulse wave velocity becomes an information source for obtaining an index useful for health care.

The blood pressure calculating unit 19 is a processing unit that calculates blood pressure. In one aspect, the blood pressure calculating unit 19 calculates blood pressure by substituting the pulse wave velocity calculated by the propagation velocity calculating unit 18 into the following Equation (10). The following Equation (10) is an example of a calculation formula of blood pressure, and blood pressure, which is an objective variable, is approximated into a linear expression having the pulse wave velocity as an explanatory variable. In the following Equation (10), "P" indicates the blood pressure and "Vp" indicates the pulse wave velocity. Further, in the following Equation (10), "A" indicates a gradient of the linear expression and "B" indicates an intercept of the linear expression, and both of these are constants.

$$P=A*Vp+B \qquad (10)$$

Different values are set for these gradient A and intercept B according to individuals. For example, the gradient A and intercept B are able to be derived by causing, together with the pulse wave velocity calculated by the blood flow index calculating apparatus 10, measured values of blood pressure measured by a manometer or the like in synchronization with the calculation of the pulse wave velocity to be input as a reference. The gradient A and intercept B of the above Equation (10) may be set by execution of regression analysis, such as the least squares method between the pulse wave velocity and the measured values of blood pressure.

The above described blood pressure is a useful index for various diagnoses. For example, if the blood pressure is high, a disease, such as high blood pressure, a kidney disease, arteriosclerosis, hyperlipidemia, or a cerebrovascular disease, is able to be diagnosed. On the contrary, if the blood pressure is low, a disease, such as cardiac failure, anemia, or massive bleeding, is able to be diagnosed. As described above, by being output to an application program for executing the various diagnoses, the blood pressure becomes an information source for obtaining an index useful for health care.

Figure 9:
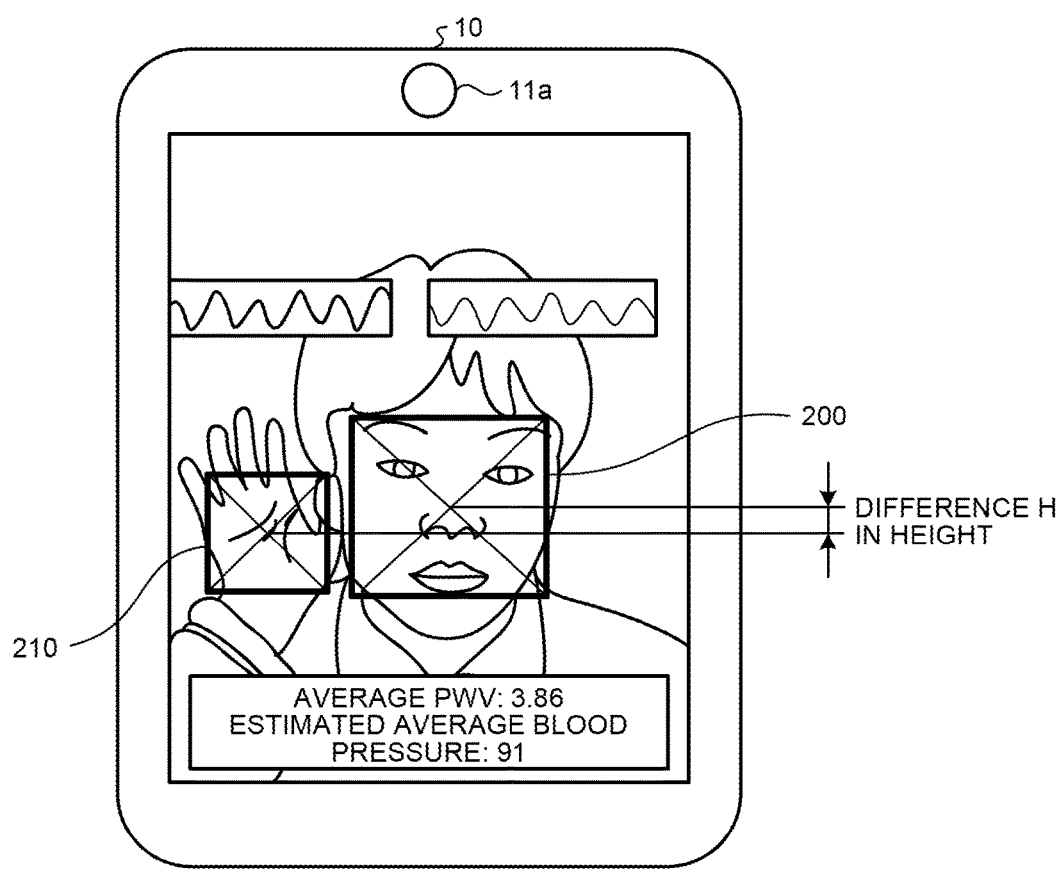
FIG. 9 is a diagram illustrating a display example of indices related to blood flow.

For example, the pulse wave velocity and blood pressure may be output to any output destination including a display device, which the blood flow index calculating apparatus 10 has and is not illustrated. FIG. 9 is a diagram illustrating a display example of indices related to blood flow. As illustrated in FIG. 9, a state where an average pulse wave velocity (PWV) has been measured to be "3.86 m/sec" and an average blood pressure has been measured to be "91 mmHg" is displayed on the liquid crystal display. Further, the pulse wave pattern of the face is displayed correspondingly with the face guide 200 and the pulse wave pattern of the hand is displayed correspondingly with the hand guide 210. As described above, a subject is able to measure the pulse wave velocity and blood pressure while operating a portable terminal, without wearing a measuring device or the like.

In addition, if a measurement program for performing measurement of vascular age, blood pressure, and the like by use of the pulse wave velocity, or a diagnosis program for diagnosing various diseases from the blood pressure is installed in the blood flow index calculating apparatus 10, an output destination of the pulse wave velocity and blood pressure may be the measurement program or the diagnosis program. Further, a server device or the like that provides the measurement program or the diagnosis program as a Web service may be the output destination. Furthermore, a terminal device used by a person concerned with a user who uses the blood flow index calculating apparatus 10, for example, a carer, a medical doctor, or the like, may be the output destination. Thereby, a monitoring service outside the hospital, for example, at home or at work, becomes possible. Needless to say, measurement results and diagnosis results of the measurement program and the diagnosis program may be displayed on terminal devices of people concerned, including the blood flow index calculating apparatus 10.

The above described functional units may be realized by the blood flow index calculating program being caused to be executed by a central processing unit (CPU), a micro processing unit (MPU), or the like. Further, the above described functional units may be realized by hard wired logic, such as an application specific integrated circuit (ASIC) or a field programmable gate array (FPGA). The above described functional units include the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, and the blood pressure calculating unit 19.

Further, a semiconductor memory element may be adopted, for example, as the above described internal memory. For example, examples of the semiconductor memory element include a video random access memory (VRAM), a random access memory (RAM), a read only memory (ROM), a flash memory, and the like. Further, instead of the internal memory, a storage device, such as a hard disk or an optical disk, may be adopted.

[Flow of Processing]

Subsequently, a flow of processing by the blood flow index calculating apparatus according to the embodiment will be described. Herein, after description of (1) a blood flow index calculating process executed by the blood flow index calculating apparatus 10, (2) a first waveform detecting process executed as a subroutine of the blood flow index calculating process will be described.

(1) Blood Flow Index Calculating Process

Figure 10:
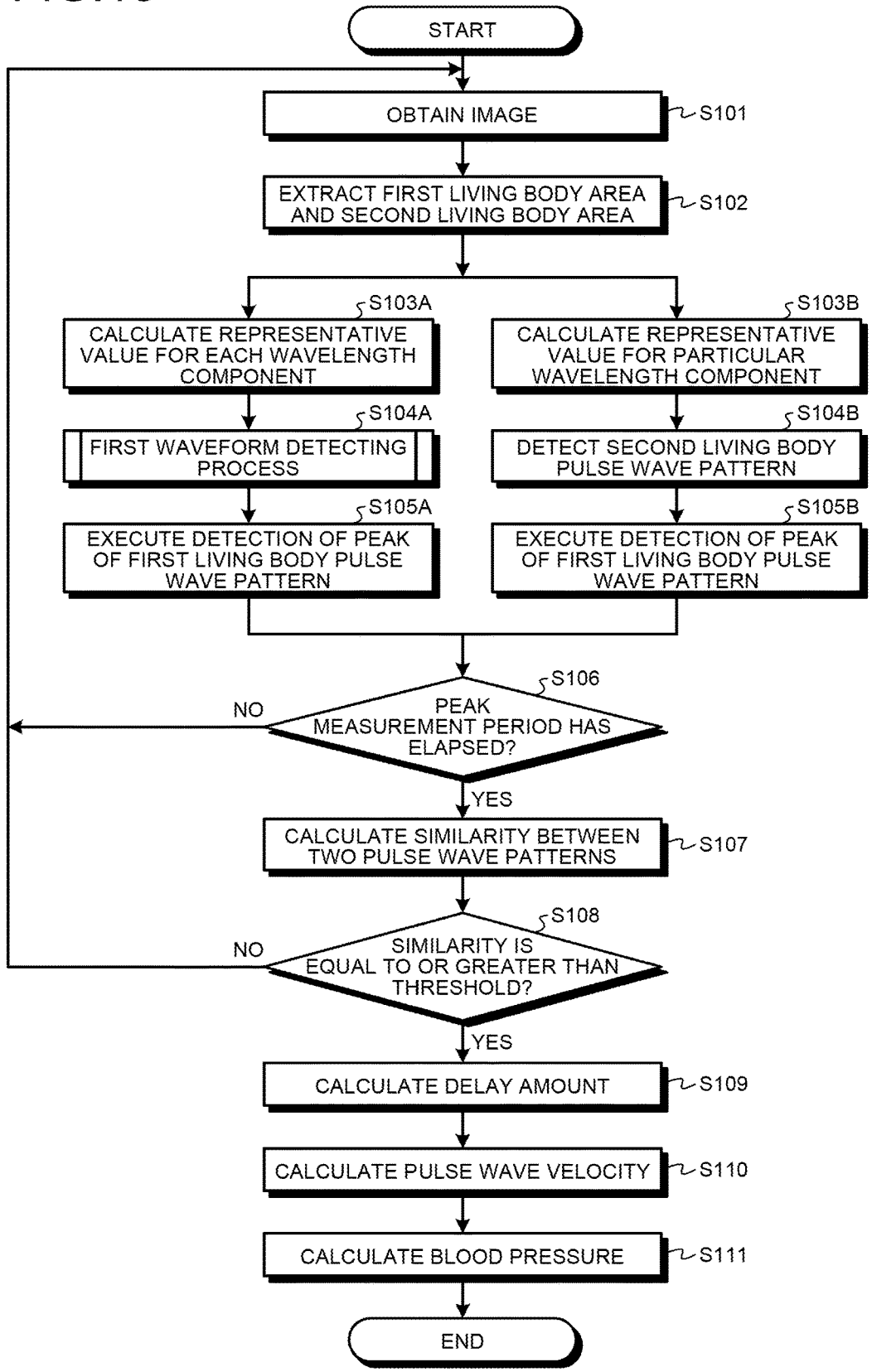
FIG. 10 is a flow chart illustrating a sequence of a blood flow index calculating process according to the first embodiment.

FIG. 10 is a flow chart illustrating a sequence of the blood flow index calculating process according to the first embodiment. This process is started by activation of the blood flow index calculating program and is a process repeatedly executed until an original image is no longer obtained by the obtaining unit 11. The blood flow index calculating process may be stopped when an interruption operation is received via an input device or the like not illustrated.

As illustrated in FIG. 10, when an original image is obtained by the obtaining unit 11 (Step S101), the area extracting unit 12 extracts a face area and a hand area from the original image obtained in Step S101 (Step S102).

Subsequently, the first representative value calculating unit 13a calculates a representative value of pixel values that pixels included in the face area extracted in Step S102 have, for each wavelength component (Step S103A). The first waveform detecting unit 14a then executes the first waveform detecting process of detecting a pulse wave pattern of the face from a signal of the representative value for each wavelength component in the face area calculated in Step S103A (Step S104A). Thereafter, the first peak detecting unit 15a executes detection of a peak of the pulse wave pattern of the face detected in Step S104A (Step S105A).

Concurrently therewith, the second representative value calculating unit 13b calculates a representative value of pixel values of the G-component that pixels included in the hand area extracted in Step S102 have (Step S103B). Subsequently, the second waveform detecting unit 14b detects a pulse wave pattern of the hand from a signal of the representative value of the G-component in the hand area calculated in Step S104B, by using a BPF or the like not illustrated (Step S104B). Thereafter, the second peak detecting unit 15b executes detection of a peak of the pulse wave pattern of the hand detected in Step S104B (Step S105B).

After the processing of these Step S105A and Step S105B is ended, the similarity calculating unit 16 determines whether or not a period in which detection of peaks from the pulse wave pattern of the face and the pulse wave pattern of the hand is executed has gone over a predetermined peak measurement period (Step S106).

If the peak measurement period has not elapsed (Step S106: No), the process returns to Step S101, and the processing up to the above described Step S105A and Step S105B is repeatedly executed.

Thereafter, if the peak measurement period has elapsed (Step S106: Yes), the similarity calculating unit 16 calculates a similarity between the pulse wave pattern of the face and the pulse wave pattern of the hand, for example, a difference between averages of cycles of peaks (Step S107). If the similarity is less than a threshold (Step S108: No), the process returns to Step S101, and the processing up to the above described Step S107 is repeatedly executed.

If the similarity is equal to or greater than the threshold (Step S108: Yes), the delay amount calculating unit 17 calculates a delay amount Td, which is a time difference between the peaks of the pulse wave pattern of the face and the pulse wave pattern of the hand (Step S109).

Subsequently, the propagation velocity calculating unit 18 calculates the pulse wave velocity Vp by substituting, together with the delay amount calculated in Step S109, the distance difference L set in the internal memory, into the above Equation (9) (Step S110). Further, the blood pressure calculating unit 19 calculates the blood pressure by substituting the pulse wave velocity Vp calculated in Step S110 into the above Equation (10) (Step S111).

Finally, after the pulse wave velocity Vp calculated in Step S110 and the blood pressure P calculated in Step S111 have been output to a predetermined output destination, a peak time that has been registered in the internal memory is deleted, and the process is ended. Although the case where the process is ended after calculation of the blood pressure has been described as an example, the process may return to Step S101 and output of the pulse wave velocity Vp and blood pressure P may be repeatedly executed.

In the flow chart illustrated in FIG. 10, the case where the processing of Step S103A to Step S105A and the processing of Step S103B to Step S105B are concurrently executed has been illustrated as an example, these may be executed serially. In that case, either the processing of Step S103A to Step S105A or the processing of Step S103B to Step S105B may be executed first or later.

In the flow chart illustrated in FIG. 10, the case where both the pulse wave velocity and blood pressure are calculated has been illustrated as an example, but not necessarily both are calculated, and calculation may be performed targeting any one of them.

(2) First Waveform Detecting Process

Figure 11:
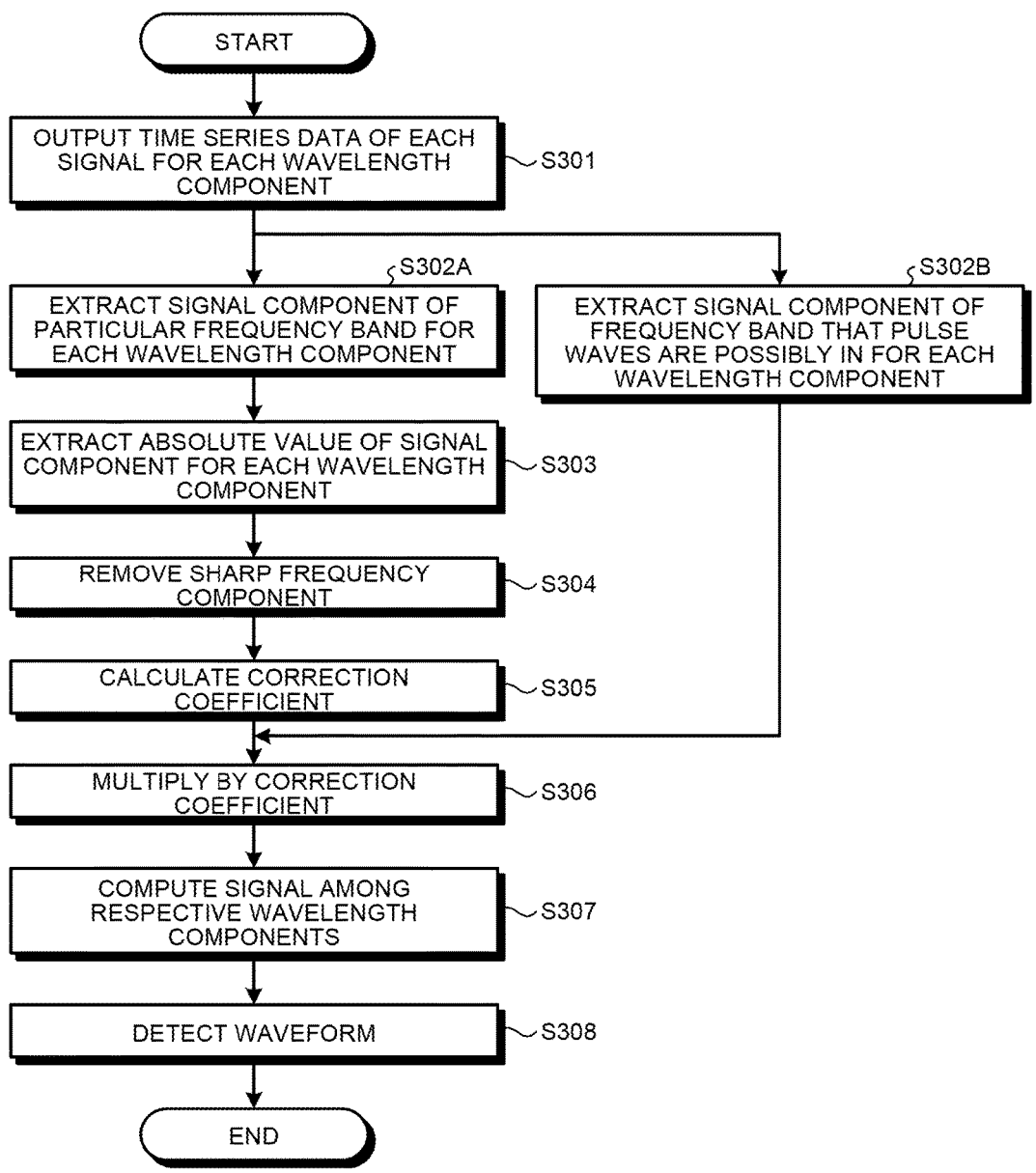
FIG. 11 is a flow chart illustrating a sequence of a first waveform detecting process according to the first embodiment.

FIG. 11 is a flow chart illustrating a sequence of the first waveform detecting process according to the first embodiment. This process is a process corresponding to Step S104A illustrated in FIG. 10, and the process is activated when a representative value of pixel values that pixels included in the face area have is calculated for each wavelength component.

As illustrated in FIG. 11, the first representative value calculating unit 13a outputs the R-signal, which is the representative value of the R-component of the face area, to the BPF 142R and BPF 146R and outputs the G-signal, which is the representative value of the G-component of the face area, to the BPF 142G and BPF 146G (Step S301).

Subsequently, the BPF 142R extracts a signal component of a particular frequency band of the R-signal, for example, a frequency band of equal to or greater than 0.05 Hz and equal to or less than 0.3 Hz, and the BPF 142G extracts a signal component of the particular frequency band of the G signal (Step S302A).

The extracting unit 143R extracts an absolute value of a strength of the signal component of the particular frequency band of the R-signal, and the extracting unit 143G extracts an absolute value of a strength of the signal component of the particular frequency band of the G-signal (Step S303).

Thereafter, the LPF 144R executes a smoothing process of causing time series data of the absolute values of the strengths of the particular frequency band of the R-signal to respond to time change, and the LPF 144G executes a smoothing process of causing time series data of the absolute values of the strengths of the particular frequency band of the G-signal to respond to time change (Step S304).

Subsequently, the calculating unit 145 calculates a correction coefficient k by executing division, "G'n/R'n", of dividing the absolute value G'n of the strength of the particular frequency band of the G-signal output by the LPF 144G, by the absolute value R'n of the strength of the particular frequency band of the R-signal output by the LPF 144R (Step S305).

Concurrently with the processing of the above described Step S205A, the BPF 146R extracts a signal component of a pulse wave frequency band of the R-signal, for example, a frequency band of equal to or greater than 0.5 Hz and equal to or less than 4 Hz, and the BPF 146G extracts a signal component of the pulse wave frequency band of the G-signal (Step S302B).

Thereafter, the multiplying unit 147 multiplies the signal component of the pulse wave frequency band of the R-signal extracted in Step S302B, by the correction coefficient k calculated in Step S305 (Step S306). Thereafter, the computing unit 148 executes computation, "Gs−k*Rs", of subtracting the signal component of the pulse wave frequency band of the R-signal that has been multiplied by the correction coefficient k in Step S306, from the signal component of the pulse wave frequency band of the G-signal extracted in Step S302B (Step S307), outputs the pulse wave pattern of the face to the first peak detecting unit 15a (Step S308), and ends the process.

Effects of First Embodiment

As described above, the blood flow index calculating apparatus 10 according to this embodiment detects pulse waves of the face and pulse waves of the hand from an image in which the face and the hand of a subject have been simultaneously shot, and calculates an index related to blood flow from a delay amount, which is a time difference between patterns of the pulse waves of the face and pulse waves of the hand. Therefore, the blood flow index calculating apparatus 10 according to this embodiment is able to calculate the pulse wave velocity and blood pressure, in addition to the delay amount, by making use of hardware that a general portable terminal has. Therefore, by the blood flow index calculating apparatus 10 according to the embodiment, without extra hardware, an index related to blood flow is able to be calculated.

Second Embodiment

Although the embodiment related to the disclosed apparatus has been described above, the present invention may be implemented in various different modes, other than the above described embodiment. Thus, hereinafter, other embodiments included in the present invention will be described.

[Correction of Blood Pressure]

In the above described first embodiment, the case where the blood pressure calculated by the blood pressure calculating unit 19 is output as it is has been described as an example, but the blood flow index calculating apparatus 10 corrects the value of the blood pressure according to the magnitude of the difference in height between the face and the hand, for example. That is, if measurement is performed at a position 10 cm higher than the heart, it becomes difficult for the blood to flow and the value becomes about 8 mmHg lower than a value correctly measured, while the opposite is true when the position is lower than the heart. Therefore, if the position of the hand is higher than the position of the heart, the blood pressure calculated by the blood pressure calculating unit 19 is corrected to a value higher than the calculated value. On the contrary, if the position of the hand is lower than the position of the heart, the blood pressure calculated by the blood pressure calculating unit 19 is corrected to a value lower than the calculated value. For example, by use of the following Equation (11), the blood pressure may be corrected. In the following Equation (11), "P" is the blood pressure (mmHg), "H" is the difference in height between the face and the hand (cm), and "P'" is the corrected blood pressure (mmHg). Of these, the difference H between heights of the face and hand may be calculated by finding a difference between heights of centers of gravity of the face guide 200 and hand guide 210.

$$P' = P + 0.8H \quad (11)$$

[Determination of Measurability]

In the above described first embodiment, the case where the calculation of a delay amount and the processing thereafter are stopped according to the magnitude of the similarity has been described as an example, but whether or not the processing is to be stopped may be determined according to a factor other than the magnitude of the similarity. For example, the blood flow index calculating apparatus 10 associates one of the peaks included in the pulse wave pattern of the face with one of the peaks included in the pulse wave pattern of the hand, the associated peaks having the shortest time interval between each other. The similarity calculating unit 16 executes the calculation of a delay amount and the processing thereafter, if the sampling times that each pair of the peaks associated between the pulse wave pattern of the face and pulse wave pattern of the hand has are in the order of the peak of the pulse wave pattern of the face and the peak of the pulse wave pattern of the hand. If the number of the respective pairs of the peaks is not in a predetermined range, for example, is less than a number paced at 30 bpm, or greater than a number paced at 240 bpm, even if there is consistency in the order, the calculation of the delay amount and the processing thereafter are not executed.

[Separation and Integration]

Each element in the configuration of each device illustrated in the drawings is not necessarily physically configured as illustrated in the drawings. That is, a specific mode of separation and integration of the respective devices is not limited to those illustrated in the drawings, and all or a part thereof may be configured to be functionally or physically separated or integrated in arbitrary units depending on various loads, use situations, and the like. For example, the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, or the blood pressure calculating unit 19 may be connected via a network as an external device of the blood flow index calculating apparatus 10. Further, the above described functions of the blood flow index calculating apparatus 10 may be realized by the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, or the blood pressure calculating unit 19 being respectively included in another device, being connected to a network, and working with another.

[Blood Flow Index Calculating Program]

Further, the various processes described in the above embodiments may be realized by executing a program, which has been prepared beforehand, by a computer, such as a personal computer or a work station. Hereinafter, by use of FIG. 12, an example of a computer that executes the blood flow index calculating program having the same functions as the above described embodiments will be described.

Figure 12:
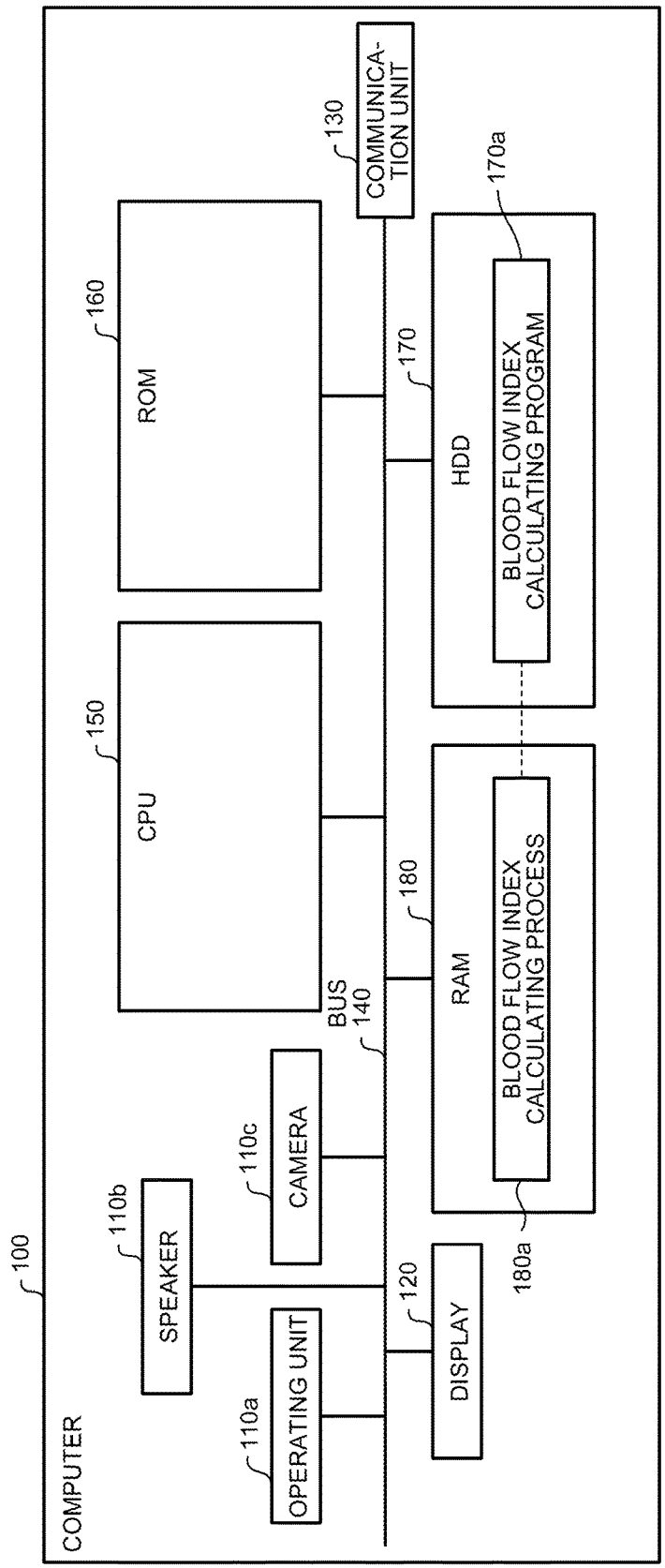
FIG. 12 is a diagram for description of an example of a computer that executes blood flow index calculating programs according to the first embodiment and a second embodiment.

FIG. 12 is a diagram for description of an example of a computer that executes the blood flow index calculating program according to the first embodiment and a second embodiment. As illustrated in FIG. 12, a computer 100 has an operating unit 110a, a speaker 110b, a camera 110c, a display 120, and a communication unit 130. Further, this computer 100 has a CPU 150, a ROM 160, an HDD 170, and a RAM 180. These units 110 to 180 are connected to one another via a bus 140.

In the HDD 170, as illustrated in FIG. 12, a blood flow index calculating program 170a, which demonstrates the same functions as those of the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, and the blood pressure calculating unit 19, is stored beforehand. Integration or separation within this blood flow index calculating program 170a may be performed as appropriate, similarly to the respective elements of the configurations of the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, and the blood pressure calculating unit 19, which are illustrated in FIG. 1. That is, not all of the data stored in the HDD 170 need to be always stored in the HDD 170, and only data needed for the processing may be stored in the HDD 170.

The CPU 150 reads the blood flow index calculating program 170a from the HDD 170 and expands it into the RAM 180. Thereby, as illustrated in FIG. 12, the blood flow index calculating program 170a functions as a blood flow index calculating process 180a. This blood flow index calculating process 180a expands various data read out from the HDD 170 into an area assigned to itself on the RAM 180 as appropriate, and executes, based on the expanded various data, various processes. The blood flow index calculating process 180a includes the processes executed by the obtaining unit 11, the area extracting unit 12, the first representative value calculating unit 13a, the second representative value calculating unit 13b, the first waveform detecting unit 14a, the second waveform detecting unit 14b, the first peak detecting unit 15a, the second peak detecting unit 15b, the similarity calculating unit 16, the delay amount calculating unit 17, the propagation velocity calculating unit 18, and the blood pressure calculating unit 19, which are illustrated in FIG. 1, for example, the processes illustrated in FIG. 10 and FIG. 11. Not all of the respective processing units virtually realized on the CPU 150 always need to operate on the CPU 150, and only the processing units needed in a process may be virtually realized.

The above described blood flow index calculating program 170a is not necessarily stored in the HDD 170 or ROM 160 from the beginning. For example, each program is stored in a "portable physical medium", such as a flexible disk, the so-called FD, a CD-ROM, a DVD disk, a magneto-optical disk, or an IC card, which is inserted into the computer 100. The computer 100 then may obtain the respective programs from these portable physical media and execute the programs. Further, each program may be stored in another computer, a server device, or the like, which is connected to the computer 100 via a public network, the Internet, a LAN, a WAN, or the like, and the computer 100 may obtain the program from any of them and execute the obtained program.

According to an embodiment, an index related to blood flow is able to be calculated without extra hardware.

All examples and conditional language provided herein are intended for the pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A blood flow index calculating method comprising:
obtaining, by a camera, an image capturing a first site of a living body and a second site of the living body, the first site being a part of the living body of a subject, and the second site being a site different from the first site;
extracting an area of the first site of the living body and an area of the second site of the living body, the areas being included in the image, by a processor;
detecting a pulse wave pattern of the first site of the living body from the area of the first site of the living body and detecting a pulse wave pattern of the second site of the living body from the area of the second site of the living body, by the processor;
first calculating a delay amount between the pulse wave pattern of the first site of the living body and the pulse wave pattern of the second site of the living body, by the processor; and
second calculating an index related to blood flow by using the delay amount, by the processor, wherein the detecting includes:
extracting a component of a particular frequency band other than a frequency band that pulse waves are possibly in among respective wavelength components, for each of the wavelength components, by the processor, the particular frequency band being any frequency band other than a frequency band that pulse waves are possibly in;
calculating a correction coefficient for minimizing a component of the particular frequency band when a difference between signals of representative values of the respective wavelength components is computed by comparison between magnitudes of the components of the particular frequency band of the respective wavelength components, and wherein the component of the particular frequency band is minimized by the correction coefficient after the calculating, by the processor;
multiplying a signal value of at least one signal having the representative values as the respective wavelength components by the correction coefficient, by the processor; and
detecting a waveform of a signal in which the components of the particular frequency band have been offset with one another by calculation of the difference between the signals of the representative values of the respective wavelength components after the multiplication by the correction coefficient, by the processor.

2. The blood flow index calculating method according to claim 1, further including third calculating a similarity between the pulse wave pattern of the first site of the living body and the pulse wave pattern of the second site of the living body, by the processor, wherein
the first calculating includes executing the calculation of the delay amount when the similarity is equal to or greater than a predetermined threshold, by the processor.

3. The blood flow index calculating method according to claim 2, wherein the third calculating includes calculating the similarity by using a cross correlation function, by the processor.

4. The blood flow index calculating method according to claim 2, wherein the third calculating includes calculating a difference between a cycle of peaks obtained from the pulse wave pattern of the first site of the living body and a cycle of peaks obtained from the pulse wave pattern of the second site of the living body as the similarity, by the processor.

5. A non-transitory computer-readable recording medium storing a blood flow index calculating program that causes a computer to execute a process comprising:
obtaining, by a camera, an image capturing a first site of a living body and a second site of the living body, the first site being a part of the living body of a subject, and the second site being a site different from the first site;

extracting an area of the first site of the living body and an area of the second site of the living body, the areas being included in the image;
detecting a pulse wave pattern of the first site of the living body from the area of the first site of the living body and detecting a pulse wave pattern of the second site of the living body from the area of the second site of the living body;
first calculating a delay amount between the pulse wave pattern of the first site of the living body and the pulse wave pattern of the second site of the living body; and
second calculating an index related to blood flow by using the delay amount wherein the detecting includes:
extracting a component of a particular frequency band other than a frequency band that pulse waves are possibly in among respective wavelength components, for each of the wavelength components, the particular frequency band being any frequency band other than a frequency band that pulse waves are possibly in;
calculating a correction coefficient for minimizing a component of the particular frequency band when a difference between signals of representative values of the respective wavelength components is computed by comparison between magnitudes of the components of the particular frequency band of the respective wavelength components, and wherein the component of the particular frequency band is minimized by the correction coefficient after the calculating;
multiplying a signal value of at least one signal having the representative values as the respective wavelength components by the correction coefficient; and
detecting a waveform of a signal in which the components of the particular frequency band have been offset with one another by calculation of the difference between the signals of the representative values of the respective wavelength components after the multiplication by the correction coefficient.

6. The non-transitory computer-readable recording medium according to claim 5, wherein
the process further includes third calculating a similarity between the pulse wave pattern of the first site of the living body and the pulse wave pattern of the second site of the living body, and
the first calculating includes executing the calculation of the delay amount when the similarity is equal to or greater than a predetermined threshold.

7. The non-transitory computer-readable recording medium according to claim 6, wherein the third calculating includes calculating the similarity by using a cross correlation function.

8. The non-transitory computer-readable recording medium according to claim 6, wherein the third calculating includes calculating a difference between a cycle of peaks obtained from the pulse wave pattern of the first site of the living body and a cycle of peaks obtained from the pulse wave pattern of the second site of the living body as the similarity.

9. A blood flow index calculating apparatus comprising:
a processor configured to execute a process including:
obtaining, by a camera, an image capturing a first site of a living body and a second site of the living body, the first site being a part of the living body of a subject, and the second site being a site different from the first site;
extracting an area of the first site of the living body and an area of the second site of the living body, the areas being included in the image;
detecting a pulse wave pattern of the first site of the living body from the area of the first site of the living body and detecting a pulse wave pattern of the second site of the living body from the area of the second site of the living body;
first calculating a delay amount between the pulse wave pattern of the first site of the living body and the pulse wave pattern of the second site of the living body; and
second calculating an index related to blood flow by using the delay amount, wherein the detecting includes:
extracting a component of a particular frequency band other than a frequency band that pulse waves are possibly in among respective wavelength components, for each of the wavelength components, the particular frequency band being any frequency band other than a frequency band that pulse waves are possibly in;
calculating a correction coefficient for minimizing a component of the particular frequency band when a difference between signals of representative values of the respective wavelength components is computed by comparison between magnitudes of the components of the particular frequency band of the respective wavelength components, and wherein the component of the particular frequency band is minimized by the correction coefficient after the calculating;
multiplying a signal value of at least one signal having the representative values as the respective wavelength components by the correction coefficient; and
detecting a waveform of a signal in which the components of the particular frequency band have been offset with one another by calculation of the difference between the signals of the representative values of the respective wavelength components after the multiplication by the correction coefficient.

10. The blood flow index calculating apparatus according to claim 9, wherein
the process further includes third calculating a similarity between the pulse wave pattern of the first site of the living body and the pulse wave pattern of the second site of the living body, and
the first calculating includes executing the calculation of the delay amount when the similarity is equal to or greater than a predetermined threshold.

11. The blood flow index calculating apparatus according to claim 10, wherein the third calculating includes calculating the similarity by using a cross correlation function.

12. The blood flow index calculating apparatus according to claim 10, wherein the third calculating includes calculating a difference between a cycle of peaks obtained from the pulse wave pattern of the first site of the living body and a cycle of peaks obtained from the pulse wave pattern of the second site of the living body as the similarity.

* * * * *